(12) United States Patent
Bar-Cohen et al.

(10) Patent No.: US 11,376,424 B2
(45) Date of Patent: Jul. 5, 2022

(54) IMPLANTED ELECTRICAL LEAD FOR PACEMAKER

(71) Applicants: Children's Hospital Los Angeles, Los Angeles, CA (US); University of Southern California, Los Angeles, CA (US)

(72) Inventors: Yaniv Bar-Cohen, South Pasadena, CA (US); Gerald Loeb, South Pasadena, CA (US); Li Zhou, Los Angeles, CA (US); Xiao Yun, Los Angeles, CA (US)

(73) Assignees: CHILDREN'S HOSPITAL LOS ANGELES, Los Angeles, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 223 days.

(21) Appl. No.: 15/563,532

(22) PCT Filed: Mar. 31, 2016

(86) PCT No.: PCT/US2016/025387
§ 371 (c)(1),
(2) Date: Sep. 29, 2017

(87) PCT Pub. No.: WO2016/161189
PCT Pub. Date: Oct. 6, 2016

(65) Prior Publication Data
US 2018/0085571 A1    Mar. 29, 2018

Related U.S. Application Data

(60) Provisional application No. 62/140,766, filed on Mar. 31, 2015.

(51) Int. Cl.
*A61N 1/05* (2006.01)
*A61N 1/372* (2006.01)
(Continued)

(52) U.S. Cl.
CPC ............ *A61N 1/059* (2013.01); *A61L 31/022* (2013.01); *A61L 31/10* (2013.01); *A61N 1/0587* (2013.01);
(Continued)

(58) Field of Classification Search
CPC ..... A61L 31/022; A61L 31/10; A61N 1/0587; A61N 1/059; A61N 1/37205; A61N 1/375; A61N 1/37512
See application file for complete search history.

(56) References Cited

U.S. PATENT DOCUMENTS

| | | | | |
|---|---|---|---|---|
| 2009/0082827 A1* | 3/2009 | Kveen | ................ | A61N 1/37518 607/36 |
| 2012/0089213 A1* | 4/2012 | Markham | ............. | A61M 25/09 607/115 |
| 2015/0088221 A1* | 3/2015 | Barr-Cohen | ........... | A61N 1/362 607/33 |

FOREIGN PATENT DOCUMENTS

WO    WO-2014182948 A2 *  11/2014

* cited by examiner

*Primary Examiner* — Amanda K Hulbert
(74) *Attorney, Agent, or Firm* — Moazzam & Associates, LLC (57) ABSTRACT

An open coiled pacemaker lead is provided that has improved structural stability and functional life in vivo. The open coiled lead includes an electrically conductive material that is coated or covered by a thin layer of electrically insulative material. The coated coiled lead has adequate spacing between adjacent coils, and has a lumen of sufficient diameter, to allow for infiltration of biological connective tissue onto the surface of the coated coil when maintained in vivo for a sufficient amount of time. Infiltration of the connective tissue essentially uniformly along the entire coiled lead strengthens and lengthens the functional life of the coated coil lead.

11 Claims, 8 Drawing Sheets

(51) Int. Cl.
*A61N 1/375* (2006.01)
*A61L 31/02* (2006.01)
*A61L 31/10* (2006.01)

(52) U.S. Cl.
CPC ..... *A61N 1/37205* (2013.01); *A61N 1/37512* (2017.08)

IMPLANTED ELECTRICAL LEAD FOR PACEMAKER

This application claims priority to U.S. Provisional Patent Application Ser. No. 62/140,766, filed on Mar. 31, 2015, the contents of which are hereby incorporated by reference herein in their entirety into this disclosure.

TECHNICAL FIELD

The present subject disclosure relates to the field of medical devices. More specifically, the subject disclosure relates to the use of a particular configuration for an electrical lead for a pacemaker implanted in a subject's body which exhibits greater longevity despite being exposed to the frequent motion in the body.

BACKGROUND OF THE SUBJECT DISCLOSURE

Transvenous leads have long been the standard approach to cardiac pacing. The development of smaller generators and thinner leads has enabled transvenous pacing in younger children. However, epicardial systems are still needed in select cases, including but not limited to, patients with difficult venous access, abnormal cardiac anatomy, or very small patient size. The implantation and maintenance of these epicardial systems in children remains challenging, requiring major surgery (sternotomy or thoracotomy). In addition to these invasive implantation procedures, epicardial lead systems have had inferior long-term outcomes compared to transvenous systems. Furthermore, the cosmetic impact (scarring, skeletal deformities) on those who would not have otherwise needed a thoracotomy can be profound.

In previous studies, the present inventors and their colleagues developed a micropacemaker for use in the human fetus. It is an integrated, single-chamber pacemaker that can be implanted percutaneously into the fetal chest without the need for open uterine surgery. It is designed so that the electrode is implanted into the myocardium from the epicardial surface of the heart and connected via a short, flexible lead to a housing for the electronic circuitry, all of which resides entirely within the body of the fetus rather than being connected to the mother. The fetal micropacemaker is designed to function for one to three months until delivery of the infant, whereupon a conventional epicardial pacemaker as described above would be required.

SUMMARY OF THE SUBJECT DISCLOSURE

With experience, it has become clear that the micropacemaker device and implantation scheme described above can be adapted to post-natal use. By implanting a similar device in the pericardial space via subxyphoid approach, an entire epicardial pacing system can be implanted percutaneously without the need for thoracotomy or any other surgical incisions. The general design and implantation procedure are described in previous patent applications WO 2013/151159 and WO 2014/182948, which are incorporated by reference herein in their entirety into this disclosure. The subject disclosure taught herein concerns the design and construction of a flexible open helical lead between the housing for the electronic circuitry and the pacing electrode affixed to the myocardium, which open helical lead must withstand hundreds of millions of cycles of motion from the beating heart. Immediately after implantation, the micropacemaker is initially free to orient itself in a manner that minimizes the mechanical forces to which it is exposed. The short distance between the electrode and the housing is bridged by an open helical coil made of highly elastic stainless steel (SS304) and insulated with only a thin layer of highly flexible and biocompatible polymer, for example from a polymer from the family of polyparaxylylene. One particular example is Parylene-C. The insulative material may have thickness of 5-30 um. The open helical lead is designed to induce and to mechanically complement the living connective tissue in which it becomes embedded in such a way as to distribute the motion evenly along the open helical lead so that local stresses stay below a critical threshold where the electrical conductor is at risk of fracture failure from stress fatigue.

Implanted electronic devices often require a flexible electrical lead from the electronics package to the electrode. For applications such as a cardiac pacemaker, this lead must undergo many millions of cycles of bending and stretching motion. We have designed an open helical lead comprising an electrically-conductive element in the form of an open helical coil that is not embedded in a polymeric encapsulant but is instead coated by a thin layer of electrically insulative material. In contrast to prior lead designs, the open helical lead of the present subject disclosure becomes embedded in the connective tissue that tends to form on foreign materials when implanted in the body. By carefully designing the surface and mechanical properties of the open helical lead, the connective tissue induced by its presence tends to provide support to the open helical lead so as to distribute this motion evenly along the lead. Because this connective tissue is living, it adapts to any changes in position or movement that may occur over time, preserving this supportive behavior. As such, a relatively rigid polymeric encapsulant embedding the lead is not required. As long as the local stresses on the electrical conductor and its insulating layer stay below critical limits, the open helical coil will avoid stress fatigue and should work indefinitely.

The subject disclosure has applicability to any implanted electronic medical device in which an electrode must be located at some distance from, and flexibly coupled to, an electronics package. Exemplary embodiments relate to a minimally invasive cardiac pacemaker that is located entirely within the pericardial membrane. Other applications requiring a long flex life include neural recording and stimulation interfaces with motile visceral organs such as in the gastrointestinal tract and with muscles and peripheral nerves, or where electrical leads must traverse parts of the body with high mobility such as the neck for deep brain stimulators.

Implantation and maintenance of a permanent cardiac pacing system in children remains challenging due to small patient size, structural heart defects, and growth. Epicardial pacing is usually employed, but it requires an invasive procedure for device implantation and the rate of lead failure is substantially higher than that of transvenous leads. We have developed a novel epicardial micropacemaker for neonates, children, and adults that can be implanted minimally invasively or percutaneously without the need for thoracotomy or any other surgical incisions. A short lead between the electrode and the electronics package in the pericardial space must withstand approximately 250 million cycles of complex motion over five years. Prior attempts at providing a lead with a lifetime of this length have generally failed due to the inflexible nature of the embedded lead structure. We have developed a novel lead which allows for living tissue to replace the usual polymeric support for the coiled conductor. To better understand and be able to predict the behavior of the implanted lead, we built and tested a mechanical dummy system in an adult pig model. We developed a modeling and analysis approach to extract the in vivo stress conditions on the open-coiled lead based on the orthogonal biplane video-radiographic images.

In developing the present subject disclosure, we have developed a biomechanical analysis approach to evaluate the in vivo lead performance, longevity estimation, and design optimization with the assistance of Finite Element Analysis (FEA).

Figure 4:
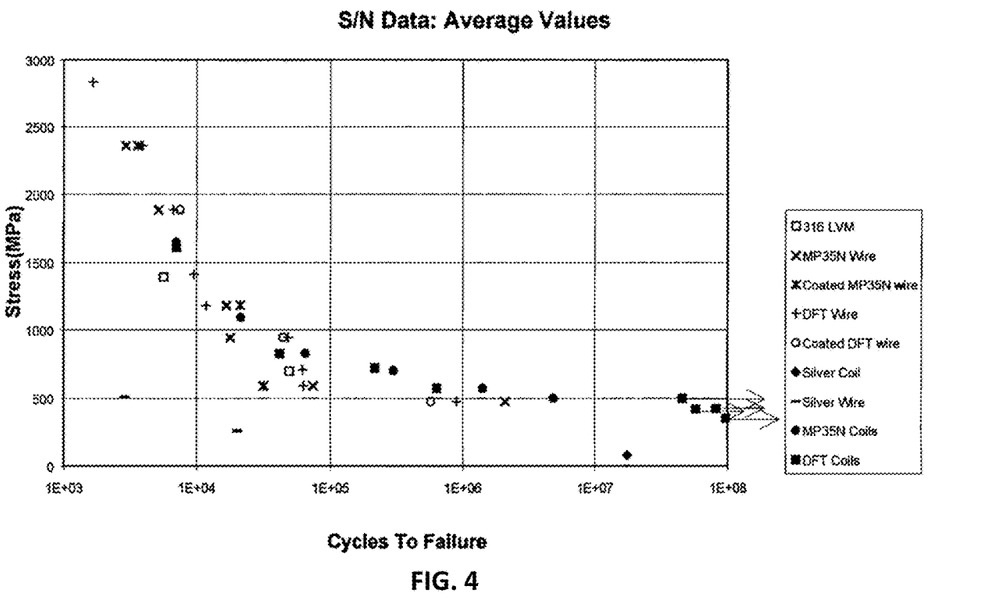
FIG. 4 shows fatigue strength-duration curves for most metal conductor materials for medical coils and is taken from P. Altman and D. Hoffmann, "Implantable electrical conductor flexure fatigue issues," in Bridging Disciplines for Biomedicine. Proceedings of the 18th Annual International Conference of the IEEE-EMBC, pp. 183-184, 1997.

The present open helical lead design benefits from the infiltrated deformable tissue matrix, rather than having the conductor embedded in a synthetic polymer that tends to degrade over time, as is currently used in the art. The stresses and bending moments are evenly distributed along the full length of the open helical coil due not only to its ability to flex as the heart beats, but also to the support provided by infiltrated connective tissue. The required lead longevity is greater than or about five years, which correlates to approximately 250 million cycles of complex motions. The fatigue failure of the metal conductor is of utmost concern for this type of electro-mechanical linkage. Therefore, the coil must be carefully designed to demonstrate it is safe to be used under in vivo loading conditions. FIG. 4 shows that helical leads made from spring-like materials will survive indefinitely (greater than 100 million cycles) if no part of the lead experiences a tensile stress above a threshold value of approximately 400 MPa=$4\times10^8$ N/m$^2$. Thus, a first challenge addressed by the present subject matter was to demonstrate that the motion of the open helical coil lead observed in vivo is well within this limit. The present subject disclosure provides data, based on a biomechanical analysis approach, showing optimization of the design, measurement of lead performance in vivo, and estimation of longevity using Finite Element Modeling (FEM) software.

BRIEF DESCRIPTION OF THE DRAWINGS

The accompanying drawings, which are incorporated in and constitute a part of this specification, illustrate embodiments of the subject disclosure and technical data supporting those embodiments, and together with the written description, serve to explain certain principles of the subject disclosure.

DETAILED DESCRIPTION OF THE SUBJECT DISCLOSURE

The following detailed description references specific embodiments of the subject disclosure and accompanying figures, including the respective best modes for carrying out each embodiment. It shall be understood that these illustrations are by way of example and not by way of limitation.

Reference will now be made in detail to various exemplary embodiments of, and data supporting, the subject disclosure, examples of which are illustrated in the accompanying drawings.

WO 2010/037557, incorporated by reference herein in its entirety into this disclosure, discloses a self-contained single-chamber micropacemaker that can be completely implanted in a fetus. The micropacemaker system was designed for implantation through a narrow (3.8 mm) cannula directly through the maternal abdomen and into the fetal chest under ultrasound guidance. Once the distal end of the introducing cannula is positioned at the fetal heart, the entire device is inserted through the cannula and the corkscrew electrode is implanted into the fetal ventricular myocardium. As the implant is deployed in the fetal chest, the myocardial electrode separates from the pulse generator/electronic circuitry with a conjoining flexible lead to accommodate the cardiac and respiratory motion.

Figure 1A:
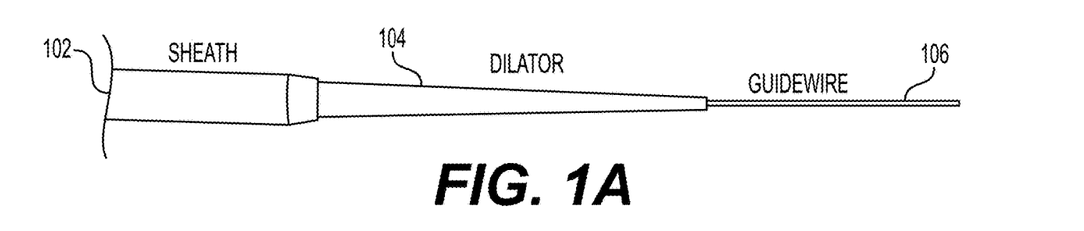
FIGS. 1A-1C depict a micropacemaker and implantation hardware suitable for use in the present subject disclosure.
Figure 1B:
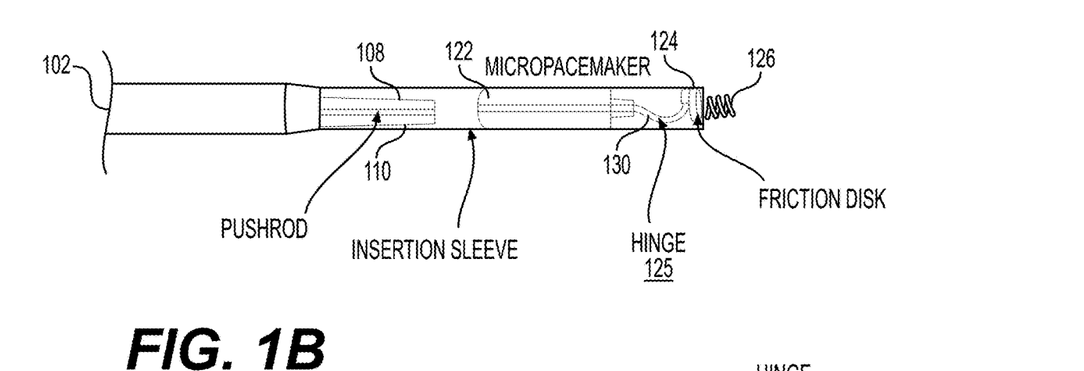

WO 2014/182948, incorporated by reference herein in its entirety into this disclosure, discloses a pacemaker lead design that alters the lead design of WO 2010/037557 by including a hinge mechanism in the flexible lead connecting the electrode to the pulse generator/electronic circuitry of the micropacemaker. The hinge causes the micropacemaker, once deployed, to automatically align parallel to the myocardium and pericardial sac with little or no strain on the pacemaker electrode or myocardial tissue. In summary, to implant the devices according to WO 2010/037557 and WO 2014/182948, after a needle is introduced into the pericardial space via subxyphoid approach, a wire is advanced into the pericardial space followed by a dilator and sheath (FIG. 1A). The fetal micropacemaker device is designed to be advanced in an insertion sleeve that allows the corkscrew electrode to be implanted directly into the epicardium (FIG. 1B). After electrode insertion, the micropacemaker is deployed into the pericardial space prior to removal of the sleeve and sheath from the body (FIG. 1C), where it assumes its resting orientation with the myocardial electrode perpendicular to the epicardial lead and parallel to the myocardium and pericardial sac. The micropacemakers and implantation methods of WO 2010/037557 and WO 2014/182948 can be applied to the needs of fetuses as well as post-natal epicardial pacing of infants, children, and adults. This is accomplished by implanting the entire pacing system (electrode, hinge (if present) flexible lead, and micropacemaker) inside the pericardial space. Percutaneous access to the pericardial space is currently used for a number of other cardiac procedures, including, but not necessarily limited to, epicardial cardiac ablations and implantation of left atrial appendage occlusion devices.

In both technologies described in the WIPO documents discussed above, after deployment, the flexible pacemaker lead will need to tolerate millions of flexions to allow for clinically useful system longevity. It is known that pacing leads are the most common source of device failure and adverse events from cardiac pacemakers and defibrillators. A pacemaker lead is required to convey electrical signals between the mechanically contracting myocardium and the rigid housing of the generator circuitry. In commercially available pacemakers, the electrodes are embedded in the endocardial or epicardial surface of the heart with the relatively large generator surgically implanted in the abdomen or chest, resulting in a long lead. The implantation scheme of the present subject disclosure, which includes a short, flexible open helical coil lead between the electrode and pulse generator/electronic circuitry, allows an opportunity to improve upon the traditional pacemaker lead designs, which have changed little over time.

The vast majority of currently used leads consist of metal conductors inside a solid sheath of elastomeric polymer. Many variations of materials and dimensions for conductors and polymers have been developed, but these leads continue to be plagued by long-term failure. Constant bending of metal electrical conductors tends to produce cumulative dislocations of their crystalline structure, resulting in loss of strength (stress fatigue) and eventual fracture, but only if local strains exceed the elastic deformation limit of the alloy. In current commercially available pacemaker leads, this tends to occur where mechanical discontinuities cause motion to be focused at one site. This can occur at anatomical impingement sites, such as the transition across the wall of the vein, near the clavicle or as the lead crosses the diaphragm. More insidiously, however, polymeric sheaths also tend to undergo chemical changes over their lifetimes, including residual cross-linking, spontaneous breakage or oxidation of covalent bonds in their long chains and absorption of water, lipids, and myriad other chemicals circulating in the body. This manifests typically as cracks in polyurethane and calcifications in silicone elastomers. Flexion motion of the polymer focuses at such heterogeneities, rapidly accelerating the local stress fatigue of both the polymer and the internal conductors.

The present subject disclosure addresses the shortcomings in conventional techniques by providing a novel open-coil lead that naturally becomes infiltrated and stabilized by living connective tissue so that the tensile (von Mises) stresses are evenly distributed and remain much lower than the threshold for plastic deformation and eventual fatigue failure.

An advancement provided by the present subject disclosure is a short, flexible open helical lead between the pulse generator/electronic circuitry of an epicardial pacemaker and the epicardial corkscrew electrode, which permits the flexible open helical lead to survive the approximately 200,000,000 or more heart beats that typically occur over five years in vivo. According to the present subject disclosure, the flexible open helical lead design has a high-strength, insulated electrical conductor wound into the form of an open helix, which becomes infiltrated by organized connective tissue. The trophic factors that stimulate and organize such connective tissues distribute stress and strain evenly along such tissues, thereby maximizing flexibility and strength. Because the flexible open helical lead does not have to cross anatomical planes, there are no significant mechanical discontinuities, and the flexible open helical lead accommodates somatic growth and cardiac motion better than current epicardial systems. This feature is in stark contrast to the polymeric encapsulation of prior pacemaker leads, which initially have uniform mechanical properties over their lengths regardless of the structures through which they pass, but which inevitably become heterogeneous as they degrade over time. As a result, once it becomes embedded in living connective tissue, the present epicardial flexible open helical lead is better suited to long-term viability than prior pacemaker leads (whether endocardial or epicardial).

Although any number of electrically conductive materials and electrically insulative materials can be used in the present open helical lead, exemplary embodiments refer to leads comprising steel (e.g., stainless steel) as the electrically conductive material and Parylene-C as the electrically insulative material. In addition, exemplary embodiments utilize a helical lead having an electrically conductive material of stainless steel that is on the order of five one-thousandths of an inch in thickness, having five to ten turns per centimeter of length, and on the order of two to three millimeters in diameter. Furthermore, the electrically insulative coating on the electrically conductive material is of sufficient thickness to insulate the lead from the general environment of the body not substantially affecting the dimensions or mechanical properties of the helical conductor. Having such a configuration allows for infiltrating connective tissue to fully encapsulate the helical lead structure over the entire surface of the helix, which is in contrast to leads known in the art, which do not allow for access of connective tissue to the helix itself.

Furthermore, regardless of the particular electrically conductive material and the electrically insulative material chosen, the open coiled lead of the present subject disclosure is designed such that the lead itself is flexible enough to bend, twist, and extend with the beating of the heart, but its stability and working life are extended by the structural support provided by the infiltrated connective tissue. The design according to the subject disclosure thus provides a biologically-enhanced structure in which both the fabricated lead and the infiltrated connective tissue provide structural stability across the entire length of the lead.

EXAMPLES

The subject disclosure will be further explained by the following Examples, which are intended to be purely exemplary of the subject disclosure and its development, and should not be considered as limiting the subject disclosure in any way.

Example 1: In Vivo Analysis of Physical Properties of Open Helical Lead

The goal of initial experiments was to demonstrate the feasibility of our epicardial micropacemaker implantation method through a sheath placed percutaneously via subxyphoid approach into the pericardial space. In addition, we sought to document the nature of the connective tissue reaction due to the device and its open helical lead.

Figure 5:
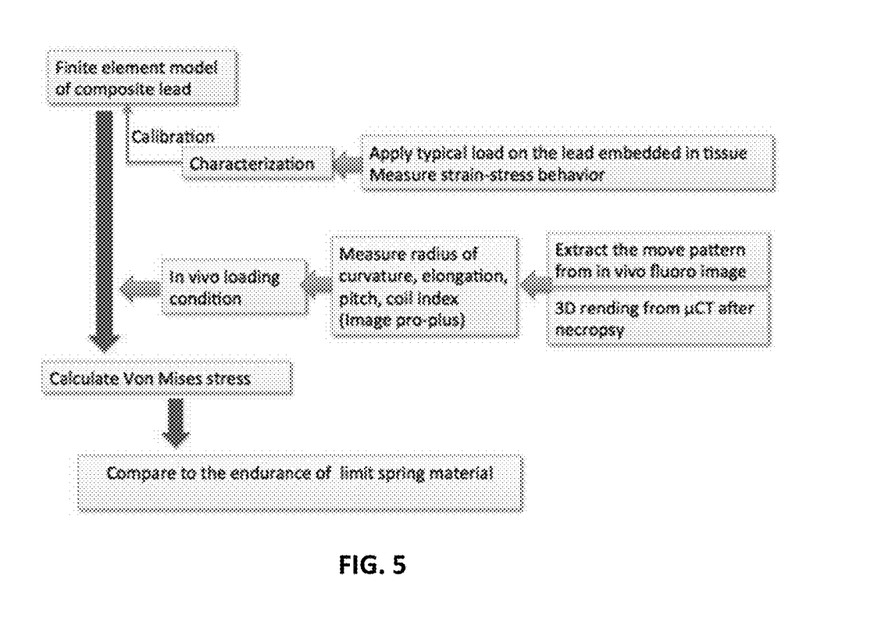
FIG. 5 shows the biomechanical analysis strategy used in the present subject disclosure that combines finite element computation and in vivo experimental testing.

We designed, built, and implanted an epicardial micropacemaker in an adult pig (approximately 30 kg). Fluoroscopic images were recorded over 8 weeks of follow-up and just before necropsy. Biplane fluoroscopic imaging of the living animal was used to determine the relative motions of the helical turns in vivo with the assistance of Image Pro-Plus® software, which was programmed to automatically track the displacement of the two ends of the implanted open helical lead in a full cycle of motion in a single plane. From this, we computed the relative motion that is dissipated in the lead. Fluoroscopy on the live animal cannot resolve the individual turns of the lead. Therefore, after the animal was euthanized, we used high-resolution micro-computed-tomography (μCT) to provide detailed resolution of the individual turns of the implanted open helical leads in a complete 3D model. The μCT machine can only accommodate a 5 cm diameter block of tissue, which is much smaller than the pig heart. By using high-resolution X-ray equipment on the whole explanted heart, we were able to obtain sufficient resolution to infer regularity of turn spacing using image analysis techniques. The computational FEM software COSMOS was used to simulate the stress distribution on the composite lead with extrapolated in vivo lead deflections and displacement as loading conditions. A flow diagram of the FEM algorithm is depicted in FIG. 5.

Figure 6A:
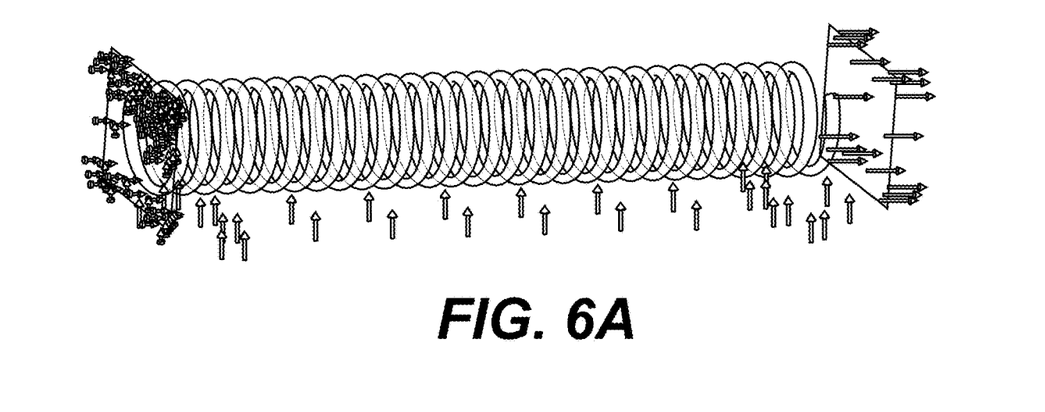
FIGS. 6A-6b show finite element modeling of the composite lead (A) and stress (B) under idealized loading conditions.
Figure 6B:
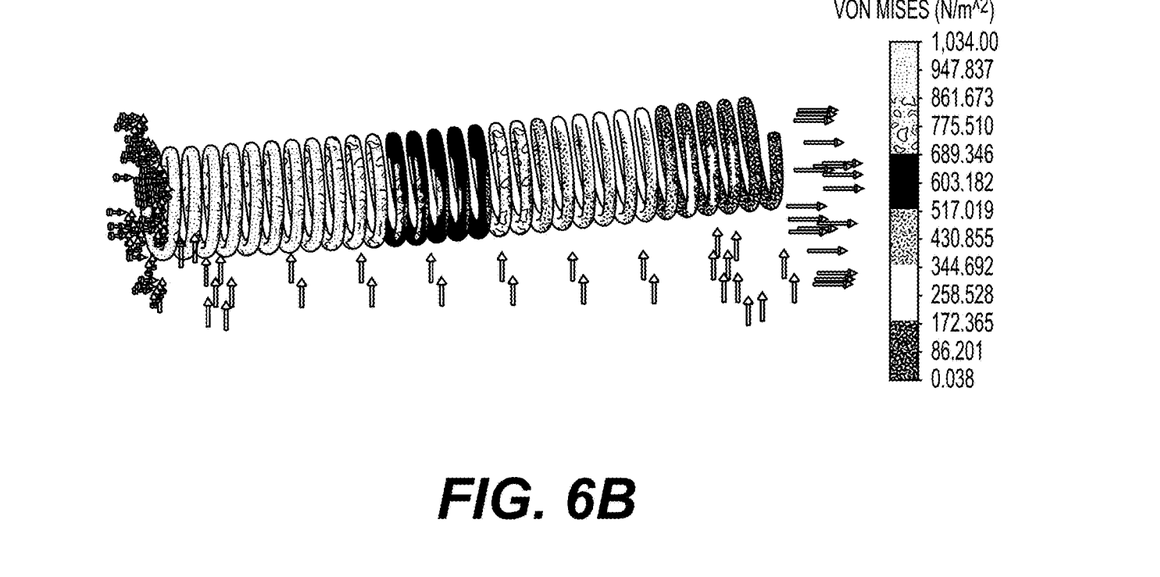

The von Mises stress distribution on the conductor lead was computed from the composite lead material under a hypothesized loading condition. The highly stressed element is believed to start yielding when its von Mises stress reaches its tested endurance limit, shown on the stress vs. lifetime performance curve that asymptotes at a threshold value of stress (FIG. 4). Preliminary FEA of our open helical lead in tissue when subjected to typical motion indicated that stresses will be many orders of magnitude below this (FIG. 6).

Pacemaker leads are usually tested in vitro where large numbers of bending cycles are applied at high speed. Doing this allows detection of manufacturing flaws, such as heterogeneities in the coiled wire or polymeric sheath. This type of in vitro testing assumes that the failure mode is simple fatigue and that the composite material (consisting of the helical wire embedded in a polymer sheath) is not influenced by the fluids and tissues of the body, which in practice is often not true. That assumption and the related accelerated life-testing methods are even less appropriate for a composite material consisting of the helical wire embedded in connective tissue. Therefore, we undertook this study to determine the effect, in vivo, of bending cycles over an extended period of time. In our preliminary animal study, the open helical leads were found to be embedded in well-organized connective tissue that formed a cylindrical encapsulating sleeve similar to the polymeric sheath of a conventional pacemaker lead.

Figure 2:
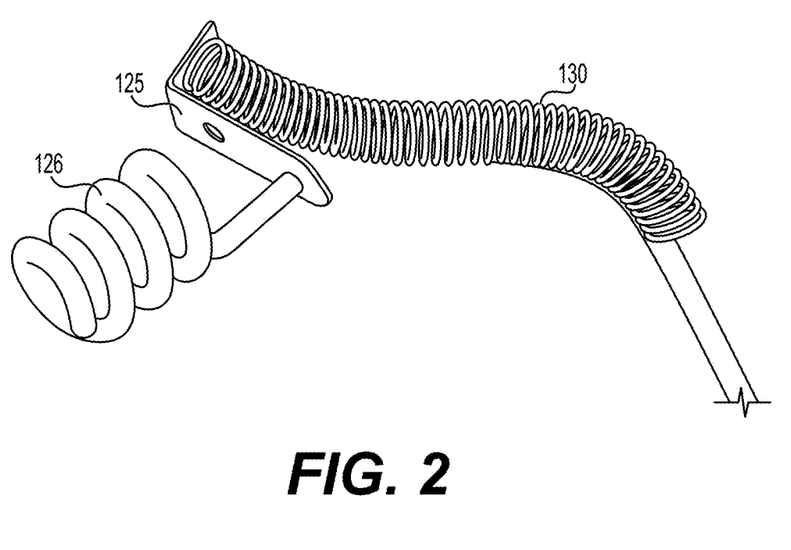
FIG. 2 shows an electrode, hinge element, and helical lead according to embodiments of the subject disclosure.
Figure 3:
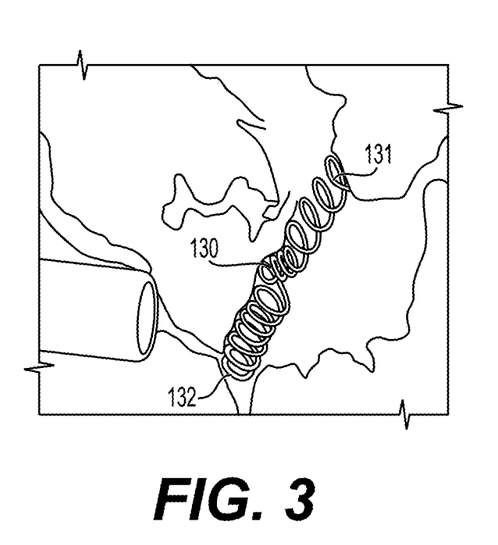
FIG. 3 shows a photograph of a micropacemaker helical lead after implantation and maintenance in vivo, showing infiltration of connective tissue on and into the wire turns of the lead.

See FIG. 2, showing an electrode 126, hinge 125, and helical lead 130 according to an embodiment of the subject disclosure; and FIG. 3, showing connective tissue infiltration of the coiled lead after implantation in vivo. It appears that the trophic factors that stimulate and organize such connective tissues distribute stress and strain evenly along such tissues, thereby maximizing flexibility and strength. Because the open helical lead does not have to cross anatomical planes, it is assumed that there are no significant mechanical discontinuities. As a result, the present data and analysis show that the epicardial flexible open helical lead of the present subject disclosure is better suited to long-term viability than currently available endocardial/epicardial pacing leads.

As indicated by FIG. 3, the pacemaker shells and flexible open helical lead coils were well-anchored by a capsule of dense connective tissue. Importantly, the open helical coil leads were found to be embedded in well-organized connective tissue that formed a cylindrical encapsulating sleeve similar to the polymeric sheath of a conventional pacemaker lead (labels 131 and 132 in FIG. 3 point out connective tissue within and around the open helical lead 130, as revealed by partial dissection). The outside of the cylindrical surface was connected to the epicardial and pericardial surfaces via loosely organized connective tissue that appeared to accommodate the relative motion of each heartbeat. In addition, the corkscrew electrodes were found to be well-anchored to the myocardium by mature connective tissue, with healthy myocytes surrounding the corkscrew and minimal inflammation. The tested micropacemakers did not employ steroid eluting elastomer, which has been demonstrated to improve performance of conventional epicardial leads. However, inclusion of steroid eluting elastomer is contemplated as part of the present subject disclosure.

Example 2: Extrapericardial Implant Procedures

Due to the history of cardiac surgery in many pediatric and congenital heart disease patients, an intact and non-adherent pericardium is not present in many patients currently requiring epicardial pacemaker procedures. In embodiments, the targets for our epicardial micropacemakers are young children with congenital complete heart block who have not previously undergone thoracotomy and pericardial instrumentation. As a result, placing a wire 106 followed by dilator 104 and sheath 102 into the relatively free pericardial space is a valid approach. However, a large proportion of epicardial pacemakers are currently implanted in patients who have previously undergone pericardial instrumentation and are likely to have adherent or absent pericardial membranes. In order to address this group of patients, the epicardial micropacemakers can be implanted without entering the pericardial space. It appears that this is possible due to our ability to visualize tissue planes immediately outside of the sheath tip using a video camera probe. For example, after placing a guide wire into the left pleural space via Tuohy needle and subxyphoid approach, the needle can be removed and a dilator and sheath can be advanced over the wire. When the sheath tip is positioned in the pleural space near the heart using fluoroscopic guidance, the camera probe can be inserted into the sheath for visualization of the external pericardial surface. The sheath tip can be advanced against an optimal implantation site on the outer pericardial surface (perpendicular to the epicardial surface), and the camera then can be removed. The micropacemaker implantation sleeve can then be inserted into the sheath and the corkscrew electrode 126 rotated into the myocardium through the pericardial layers. The device is then released into the pleural space, whereby the hinge apparatus 125 results in the micropacemaker lying parallel to the epicardial surface, but on the outside of the pericardium. We have demonstrated the feasibility of positioning the micropacemaker device on the outside of the pericardium in our preliminary pig experiment and demonstrated a connective tissue reaction around the micropacemaker that was similar to that seen with the intrapericardial device. This extrapericardial device also became fixed relative to the heart motion (by adhering to the outside pericardium) as opposed to freely moving in the pleural space. This is an apparent advantage because a freely moving device in the pleural space would result in significantly more lead stresses over time.

Example 3: Optimization of Flexible Lead

Figure 1C:
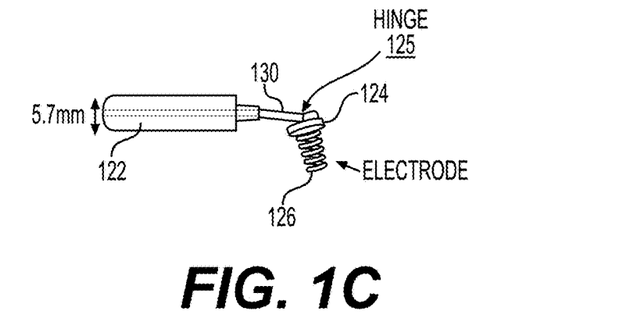
Figure 10:
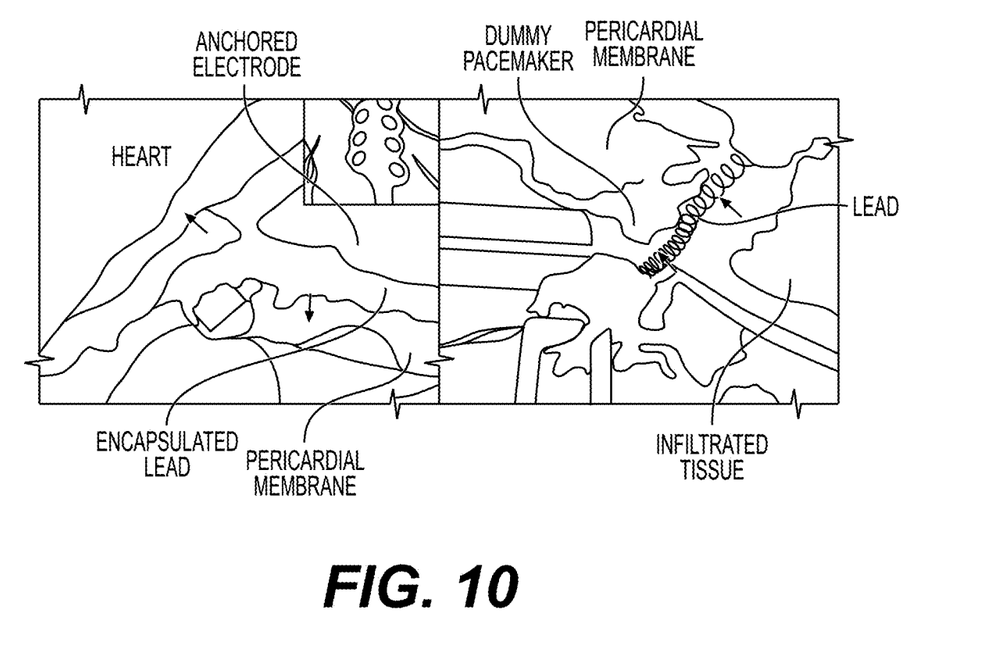
FIG. 10 shows placement of the implanted mock pacemaker with (Left) a corkscrew electrode implanted in the ventricular myocardium and (Right) a dummy pacemaker in the plural space.

During the minimally invasive implantation procedure, the open helical lead 130 must function as a combined hinge and spring, as illustrated in FIG. 1 where the open helical lead 130 is identified as performing the function of a hinge 125. At their point of mutual attachment within the friction disk 124, the open helical lead is oriented approximately perpendicularly to the axis of the helical electrode 126 that will be implanted into the myocardium from the epicardial surface. The open helical lead 130 is oriented parallel to the long axis of the cylindrical enclosure 122 that will contain the electronic circuitry of the pacemaker (here represented as a dummy epoxy cylinder 122). During implantation via the percutaneous sheath 102, the axes of the electrode 126 and circuitry enclosure 122 are held in parallel alignment by an insertion sleeve 102 that grips the friction disk 124 at its distal end. In this configuration, axial force and torque can be applied to the electrode 126 by manipulating the external end of the insertion sleeve 102 so as to screw the electrode 126 into the myocardium like a corkscrew. When the electrode 126 has become anchored, the entire micropacemaker assembly including the open helical lead 130 is expelled from the insertion sleeve 102 and into the pericardial space by the pushrod 108. The hinge 125 relaxes into its resting, straight configuration as shown in FIGS. 10 and 2, allowing the cylindrical electronics package 122 and open helical lead 130 to lie parallel to the epicardial surface of the heart while the electrode 126 remains perpendicular in the myocardium.

The open coil helical lead 130 comprises a lead material and a structure which become embedded in living connective tissue thereby forming a composite material that resists stress fatigue from frequent motion. In one exemplary embodiment, the open coil helical lead has an external diameter of 2-5 mm, a lead wire diameter of 0.1-0.3 mm, and a coil having 5-10 turns per centimeter of length. However, other sizes and configurations are possible as long as they serve the functions of creating a composite material with the connective tissue.

Currently available epicardial pacemaker leads have higher incidences of exit block, elevated thresholds with reduced battery life, and lead fracture. The hinge mechanism that we have trialed in our pig experiments appears to function well to minimize stress on tissues. In order to obtain long-term functionality of the epicardial micropacemaker system, however, the flexible open helical coil lead must accommodate millions of flexions. As described above, our epicardial micropacemaker flexible open helical lead is intended to avoid stress-risers that occur when conventional polymeric encapsulants become embrittled and fracture. Spring-like metals commonly used in pacemaker leads include stainless steel 316 LVM and MP35N (as opposed to ductile materials such as silver). FIG. 4 shows that helical leads made from spring-like materials will survive indefinitely (greater than 100 million cycles) if no part of the lead experiences a tensile stress above a threshold value of approximately 400 MPa=$4 \times 10^8$ N/m$^2$. Thus, our challenge is to demonstrate that the motion of the open helical lead observed in vivo is well within this limit. We explain this below, starting with an explanation of why more conventional methods for testing pacemaker leads are not suitable and follow with our somewhat complex alternative strategy with a demonstration of the feasibility of each step.

Modeling and Optimization of Open-Coil Lead:

After device implantation, a series of inflammatory reactions result in connective tissue formation around the flexible open helical lead. This occurs as a foreign-body reaction with standard pacemaker leads, and was demonstrated in experiments on the open helical lead by necropsy and histology. The combination of the open helical lead and the connective tissue in which it is embedded constitutes a composite material. Systematic methods such as FEM require specification of the mechanical properties of all components of the composite material and the interfaces between them. The properties of the connective tissue in and around the coil cannot be assumed to be similar to published values for tissues such as fascia or subdermis. We instead assume that the foreign body response arises as a result of the materials and movements acting over time via trophic mechanisms. These mechanisms govern the initial foreign body reaction, the proliferation and distribution of fibroblasts, and the collagen deposition on and around the open-coil and adjacent membrane. The following steps provide a strategy for FEM.

Measuring Mechanical Properties of Connective Tissue Needed to Construct FEM

The mechanical properties of the tissue-embedded open-coil lead can be inferred by obtaining stress-strain measurements for various modes of motion (tension, lateral deflection, twisting). If the tissue moves reasonably homogeneously under strain, the specific properties of the connective tissue can be calculated by subtracting similar measurements on the bare open helical lead.

FEM of Composite Lead Stresses

After determining the geometry of the helical conductor embedded in the tissue, the boundary conditions for the coil-tissue adhesion are defined by the finite friction coefficient and a limited elastic slip. Edge-biased seeding can be applied to increase model accuracy and sensitivity. Using the calculated movements, lead stresses can be modeled to compute the estimated von Mises stresses in the individual turns of the helix. FIGS. 6A and 6B show the stresses resulting from a simultaneous compression and lateral translation to the left end in a composite model example (arrows depict vectors of movement). Although the stresses on a bare coil would be evenly distributed, the tissue matrix in our tissue-embedded open-coil lead results in a smooth dissipation of stresses over the length of the coil. Note that the maximal stress above is approximately 1000 N/m$^2$, a factor of 400,000 below the threshold for plastic deformation and stress fatigue ($4 \times 10^8$ N/m$^2$) of stainless steel.

Optimization of Open-Coil Parameters (Wire Gauge, Helical Diameter, Spacing of Turns)

For a model in which the connective tissue is perfectly homogeneous, the optimal helix would be made from infinitesimally fine wire with an infinite number of turns. It would then dissipate translational and rotational motion of the ends of the helix as distributed, infinitesimal torsions along the length of the fine wire. However, such a fine wire would be easily distorted from its ideal, uniform shape by even the tiniest local forces in the connective tissue, resulting in one or more stress risers that would focus the applied motion and form a more likely failure locus. A coil made from large gauge wire and few turns would cause large forces to appear at the ends during relative motion. This would likely provoke scar tissue formation at the myocardium and perhaps even electrode dislodgement. Using FEM, we explore the effects of a range of tissue heterogeneities on various helical designs to identify the desirable range of behavior.

In Vitro Fatigue Testing of Coil Lead to Exclude Other Failure Modes

The ends of the open helical lead 130 terminate in relatively large structures: the pacemaker electronics package 122 and the corkscrew electrode 126 with the epoxy friction disk 124 that holds it in position in the insertion sleeve during implantation. In exemplary embodiments, this subassembly includes a stainless steel bracket molded into an epoxy disk that accommodates laser welds to the open helical lead and the (e.g., iridium) electrode. The entire subassembly is coated with vapor-deposited Parylene for electrical insulation. These junctions present mechanical discontinuities that could provide loci for stress failures, much as an electrical cord tends to break at the back of its connector. The connective tissue encapsulation that we observed around these junctions in our experiments should act as a strain relief. In embodiments, it can be desirable to incorporate mechanical and surface features into these terminations and the immediately adjacent portions of the open helical lead that will stimulate the deposition of connective tissue in such a manner as to distribute stresses and strains more evenly.

Example 4: Detailed Analysis Based on In Vivo Conditions

Our epicardial micropacemaker system was illustrated in FIG. 1. In this design, the corkscrew electrode 126 is implanted on the epicardial surface of the heart with placement of a miniature pulse generator in the adjacent pericardial or extra-pericardial space. Immediately after implantation, the micropacemaker is free to orient itself in a manner that minimizes the mechanical forces to which it is exposed. The short distance between the electrode and the housing is connected by an open coil spring 130 made of highly elastic stainless steel (SS304 Stainless Steel, wire diameter=152.4 µm) and insulated with a thin layer of highly flexible and biocompatible polymer Parylene C (20 µm). Our lead design intends to benefit from the infiltrated, living connective tissue matrix, rather than having the conductor embedded in a synthetic polymer that tends to degrade over time [3]. The lead 130 must survive for at least 5 years until the child is old enough to receive a conventional endovascular pacemaker. Fatigue failure of the lead is a significant risk over the expected 200 million cardiac cycles. We require a lead 130 that will adapt to the local mechanical stresses in the anatomical site and a measure of that adaptation such that we can predict its long-term performance in vivo. Helical leads made from springy metallic conductors will survive indefinitely (>100 million cycles) if no part of the lead experiences a tensile stress above a threshold value of approximately 400 MPa [8]. Thus, our challenge is to demonstrate that the motion of the lead 130 observed in vivo results in stresses at all points in the lead that stay within the endurance limit of the metal conductor. In this example, we provide a modeling approach to infer stress from radiographically observable motion of such an implanted lead in vivo.

FIG. 1A shows the design and mechanical prototype of the epicardial micropacemaker implantation system. To implant the device, a Tuohy needle is introduced under fluoroscopic guidance into the pericardial space via subxyphoid approach, a guidewire 106 is advanced into the pericardial space followed by a dilator 102 and sheath 104. The epicardial micropacemaker device is wedged into the end of an insertion sleeve 102 that allows the corkscrew electrode 126 to be implanted directly into the epicardium, as shown in FIG. 1B. After electrode insertion, the micropacemaker is deployed by a pushrod 108 into the pericardial space and the guidewire 106, sleeve 110 and sheath 102 are then removed from the body. The micropacemaker system assumes its resting orientation with the myocardial electrode perpendicular to the epicardial lead, as shown in FIG. 1C Methods Animal Study The animal study protocol was approved by the Institutional Animal Care and Use Committee at the University of Southern California. Two mechanical dummy pacemakers were implanted into an adult pig (weight: 32.7 Kg) under general anesthesia with 1.5 vol % isolfuurane. One device was completely in epicardial space and the other was placed with the electrode anchored into myocardium, but the pacing lead penetrated through the epicardial membrane to connect to the pacemaker in the extra-pericardial space. Fluoroscopy was performed at implantation and PODs #9, #35 and #56 (necropsy). In each imaging session, we recorded several cycles of cardiac motion in anterior-posterior (AP) and lateral views with Philips Veradius Utility at 15 frames per second. Necropsy was performed on the POD #56 to evaluate the implants' locations and tissue interactions by gross dissection and conventional histology (Masson's trichrome stain).

3D Reconstruction of the Implanted Lead

Data Extraction from Radiographic Still Images in Live Animal

The lead coordinates information was extracted from biplane fluoroscopic images with the image analysis software Image-Pro Plus® (MediaCybernetics). A global Cartesian coordinate system was configured as illustrated in the FIG. 7. Dimensions on each image was calibrated based on the physical size of the device.

AP and Lateral Image Frames Co-Registration

Figure 7:
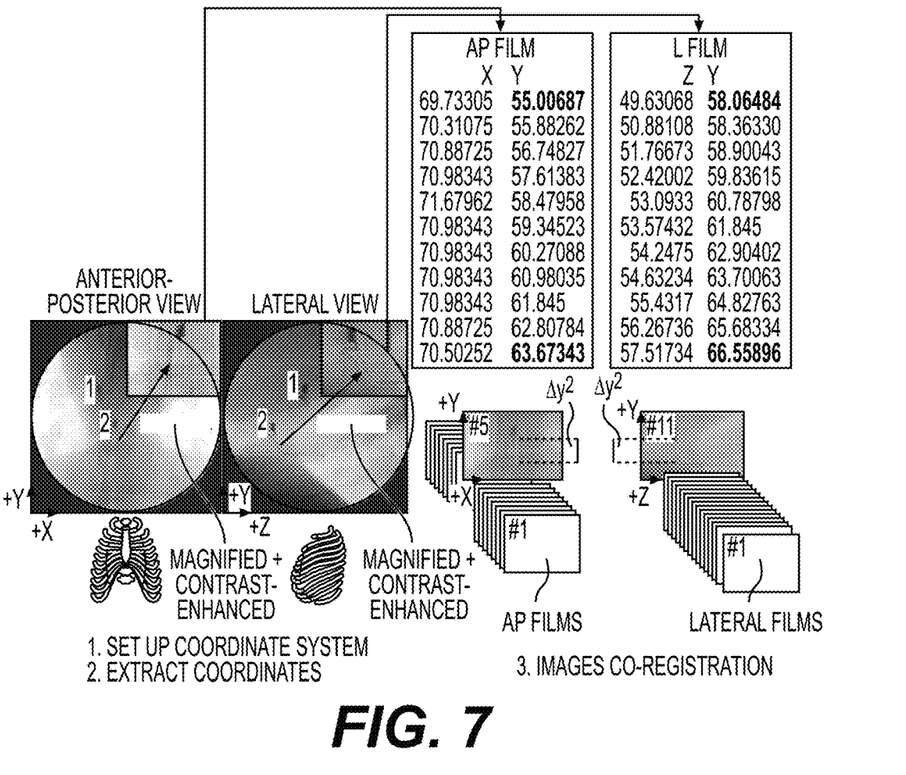
FIG. 7 shows implanted lead coordinates extraction from fluro images.

The frames of AP and lateral images were paired based on the coordinate projection on the same Y basis from the AP and lateral planes (FIG. 7). At a certain time, the projected distance (on the Y basis) between two ends of the implanted lead should be same. There, the 10 to 11 data points on the lead coil midline have been established after images co-registration.

FIG. 7 shows the implanted Lead coordinates extraction from the fluoro images (projected Anterior-Posterior and lateral views). Each image was filtered to increase the contrast. 10 to 11 points on the lead coil midline was captured. 1: 1st implant of which the corkscrew electrode was implanted directly into the epicardial surface and the entire micropacemaker device was inserted into the pericardial space. But the open-coiled lead was kinked due to the deployment. 2: 2nd implant where the electrode was again implanted directly into myocardium (in the epicardial space), but the device was deployed after the sheath had exited the pericardial space (and was therefore placed in the pleural space). The anterior-posterior (AP) and lateral fluoro images registration. The extracted y coordinates were used to derive the Δy. The criteria to pair the AP and lateral film frames is Δy1=Δy2. Otherwise, the AP film will continue to compare with the next lateral film frame. The process stops when all AP and lateral films are paired.

3D Reconstruction of the Implanted Lead

The central coil axis was 3D reconstructed with a two-step parametric function by cubic spline curve fitting in MATLAB. The two-step cubic spline interpolation ensures the lead has a continuous contour (first derivatives validated) with smooth radius of curvature (second derivatives validated) in three-dimensional space. (See FIG. 8)

Figure 8:
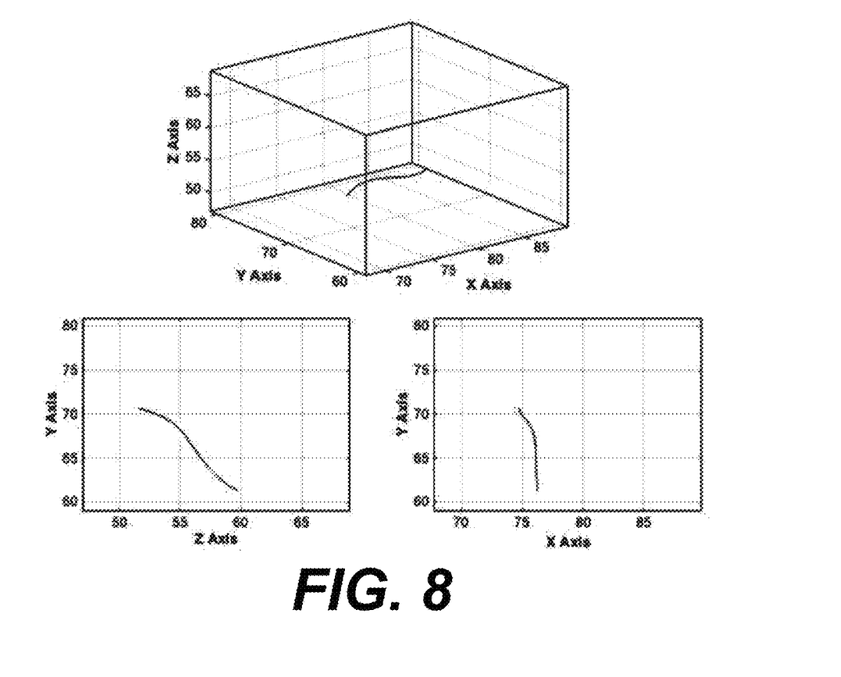
FIG. 8 shows the reconstructed implanted lead (coil midline) in three dimensional space.

FIG. 8 shows at the Top: The reconstructed implanted lead (coil midline) in three-dimensional space. Top: 3D representation of the implanted lead. The data points along the curve were curve-fitted with cubic spline interpolation. Bottom: the parametric curve of Z to Y and X to Y. The interpolated data points fit along the spline in the projected views.

The overall deflection of the open-coiled lead could be calculated from the integration of the spline. Similarly, the 3D radius curvature could be calculated with the parametric function.

Biomechanical Modeling

Analytic prediction of service stresses in the coils are generally based upon Wahl's stress analysis of close-coiled springs, where the spring index C>5 and the pitch angle $\alpha<10°$ [4]. For the spring under axial and tensile load, the analytic model can result in decent accuracy (error <5%) in predicting stresses in helical structures. The implanted pacemaker lead shares the same helical geometry and meet the criteria to apply the Wahl's analytic model, where spring index C=10 (C>5), and the pitch angle $\alpha=4.7°$ ($\alpha<10°$).

$$\delta = \frac{2\pi R_0}{\cos\alpha_0}(\sin\alpha - \sin\alpha_0)$$

$$\frac{R_0}{R} = \frac{1}{K_2}$$

$$\delta = \frac{64P(R_0)^3 n}{Gd^4} K_2$$

$$\sigma = \frac{32PR\sin\alpha}{\pi d^3}$$

$$\tau = \frac{16PR\cos\alpha}{\pi d^3}$$

where $\delta$ is the elongation/compression of the spring; $R_0$ is the coil radius before elongation; R is the coil diameter after elongation; $\alpha_0$ is the pitch angle before elongation; $\alpha$ is the pitch angle after elongation; n is number of turns; P is the tensile force; $\sigma$ is the normal stress resulted on the wire circular cross-section; d is the wire diameter; T is the shear stress (torsional stress) resulted on the wire circular cross-section.

Wahl's model excludes the effect of helix angle and the radius of curvature of the helix, which limits its application in calculating induced stresses from torsional and bending loads. For a close-coiled helical spring under bending, Meaghter et al. has developed another analytic model based on a strength of materials approach proposed by Durelli [5-7]. The analytic solution has been validated with actual spring bending tests and finite element analysis [5].

Figure 9:
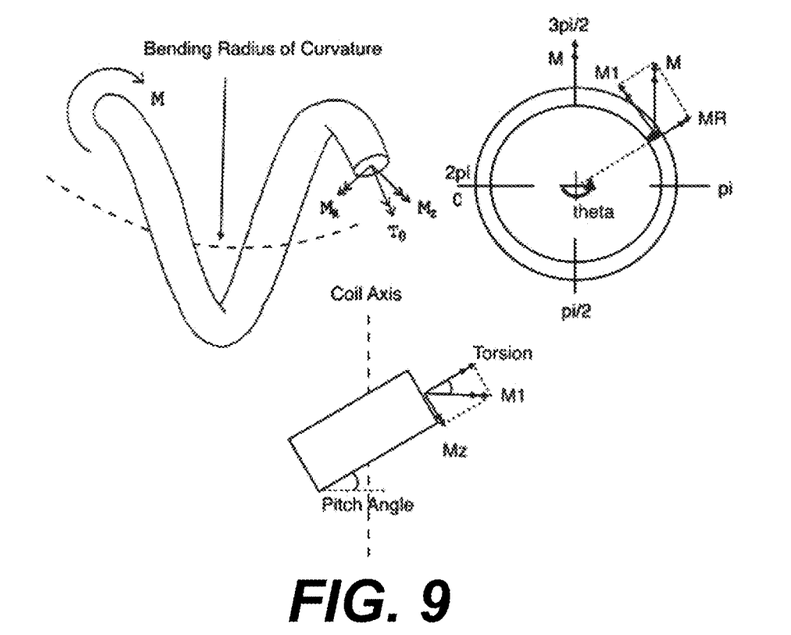
FIG. 9 shows a free body diagram of a helical spring subject to bending.

FIG. 9 shows a free body diagram of the helical spring subject to bending. M is the bending moment.

$$T_\theta = M\sin\theta\cos\alpha$$

$$M_R = M\cos\theta$$

$$M_z = M\sin\theta\sin\alpha$$

$$\frac{1}{\rho} = \frac{M}{\beta} = \frac{2EIGJ\cos\alpha\frac{L}{n}}{D\pi GJ[1+(\sin\alpha)^2] + EI(\cos\alpha)^2}$$

$$M_{res} = \sqrt{(M\cos\theta)^2 + (M\sin\theta\sin\alpha)^2}$$

-continued $$K = \frac{4\frac{D}{d}(\sec\alpha)^2 - \frac{d}{2x}}{4\frac{D}{d}(\sec\alpha)^2 - 4\frac{2x}{d}}$$

$$x = \frac{d_i}{2}\cos\gamma$$

$$\sigma = \frac{KM_{res}x}{I}$$

$$\tau = \frac{KT_\theta x}{J}$$

The curvature stress concentration factor, K, which is a function of distance from the wire axis, x, is taken from Durelli et al. For a wire with circular cross-section: $0<di<d$.

The principle stresses are calculated from:

$$\sigma_{1,2} = \frac{\sigma}{2} \pm \sqrt{\left(\frac{\sigma}{2}\right)^2 + \tau^2}$$

The von Mises stress which is useful for fatigue study is given by:

$$\sigma_{sm} = \sqrt{(\sigma_1)^2 - \sigma_1\sigma_2 + (\rho_2)^2}$$

A stand-alone MATLAB program has been developed to compute the stress condition with the governing equations above. By superimposing the normal and shear stress components resulted from bending and tensile elongation, the algorithm computes the stress condition for the implanted lead.

Results

Implant Configurations

FIG. 10 shows the placement of the implanted mock pacemaker in an adult pig after 56 days of chronic implantation. Left: the corkscrew electrode implanted in ventricular myocardium. Right: the dummy pacemaker in the pleural space. There is a moderate epicardial and myocardial fibrosis around both the cylindrical and coil portions of both devices. This fibrous connective tissue reaction was infiltrated by an also expected minimal to mild chronic inflammatory reaction associated with a benign foreign body response.

The open-coil lead of the first implanted micropacemaker dummy was inadvertently snagged on the end of the sheath during deployment, resulting in a permanent kink of the lead that made it impossible to quantify its configuration. The body of the second pacemaker was release outside the pericardium, leaving the lead to bridge through the pericardium to the myocardial electrode. This resulted in the pattern of stretch and offset of the lead that provided a useful case study for our analytical methods. The general configurations inferred from the fluoroscopic images were confirmed at necropsy (FIG. 10). The wire coils of the lead were entirely embedded in a sleeve of mature fibrous, minimally reactive connective tissue that was distinctive and separable from the surrounding membranes and structures. The helical electrode was well-anchored in the myocardium by an inner core of connective tissue with its outer surface close to apparently healthy myocytes.

Implanted Lead Geometric Deformation

Figure 11:
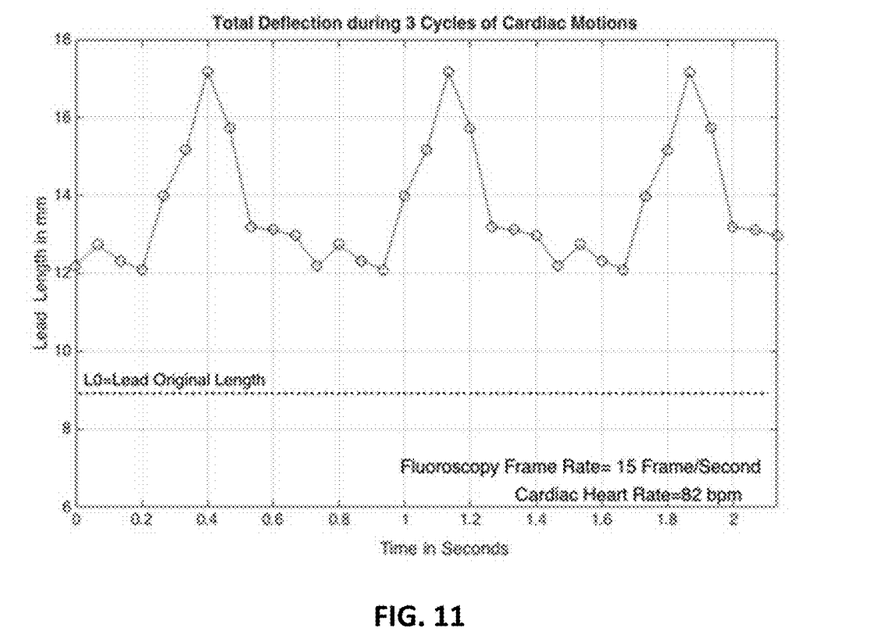
FIG. 11 shows the overall length changes of the implanted lead during three cycles of cardiac motion.

The overall deflection/elongation of the implanted lead in three full cardiac contraction cycles in pig studies is depicted in FIG. 11. The overall length is obtained from the integration of the 3D cubic spline in each frame. 11 frames represent 1 cardiac cycle. The result suggested the implanted lead was constantly under tension with a peak length of 17 mm. Given the original resting length of the lead is 10 mm, the elongation at this frame is 7 mm. The inverse of the 3D radius of curvature is plotted in FIG. 11.

Figure 12:
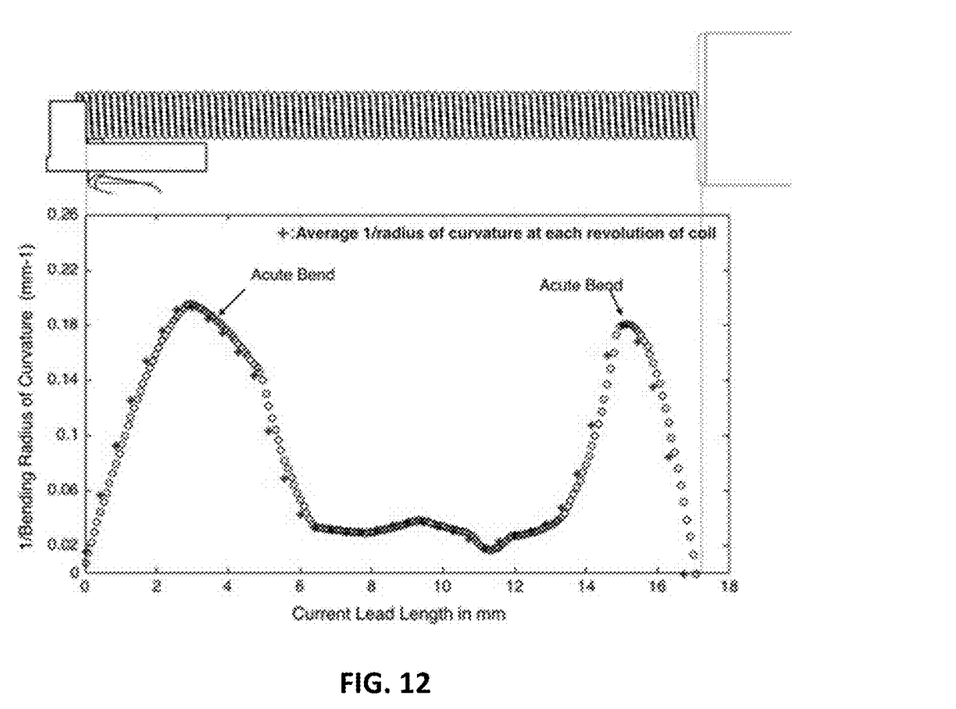
FIG. 12 shows changes of the radius of curvature along the implanted lead.

FIG. 12 shows the changes of the radius of curvature along the implanted lead at frame 7 which the lead experiences the maximum von Mises stress (see section below) and the elongation.

Stress Analysis

The computed results of the normal/shearing/von Mises (equivalent)/stresses have been stored separately in a stress matrix, of which the size is 40 by 5 by 11 by 73 by 11. Where 40 denotes an index to refer to the turn number along the spring lead (40 is the total turns of coils); 5 is an index refer to the θ angle in {0 pi/2 pi 1.5 pi 2 pi}; 11 is an index refer to the rx, representing the stress resolution on the wire cross-section, of which is from 0 to wire diameter d, the division is r/10, 73 is an index refer to the γ angle on wire cross-section, of which the resolution is κ degree around the circle (73=360/5+1); 11 is an index refer to the frame number in a sequence of lead motions. FIG. 12 presents a more pictorial indication.

Figure 13:
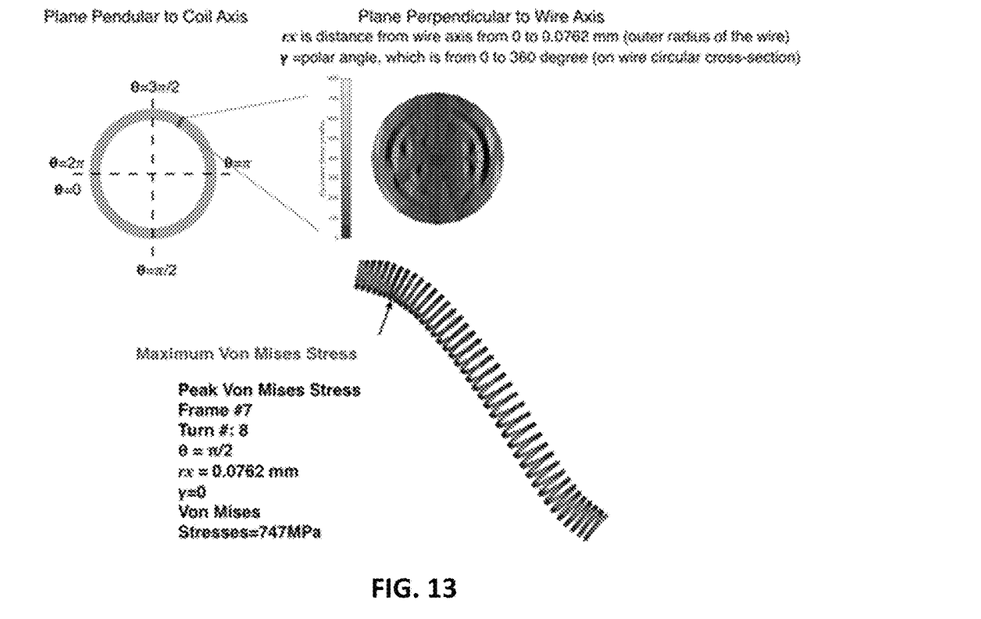
FIG. 13 shows the turn of coil experiencing the maximum von Mises Stress.

FIG. 13 shows the turn of coil experienced the maximum von Mises Stress. The spring is deformed along the interpolated coil midline in the 7th frame.

From fluoro and dissection images, this location is close to the position where the lead exits the pericardial tissue plane. The dense sleeve of connective tissues forms on both ends so that the coil is less spaced compared to the middle section of the spring lead (FIG. 13).

Figure 14:
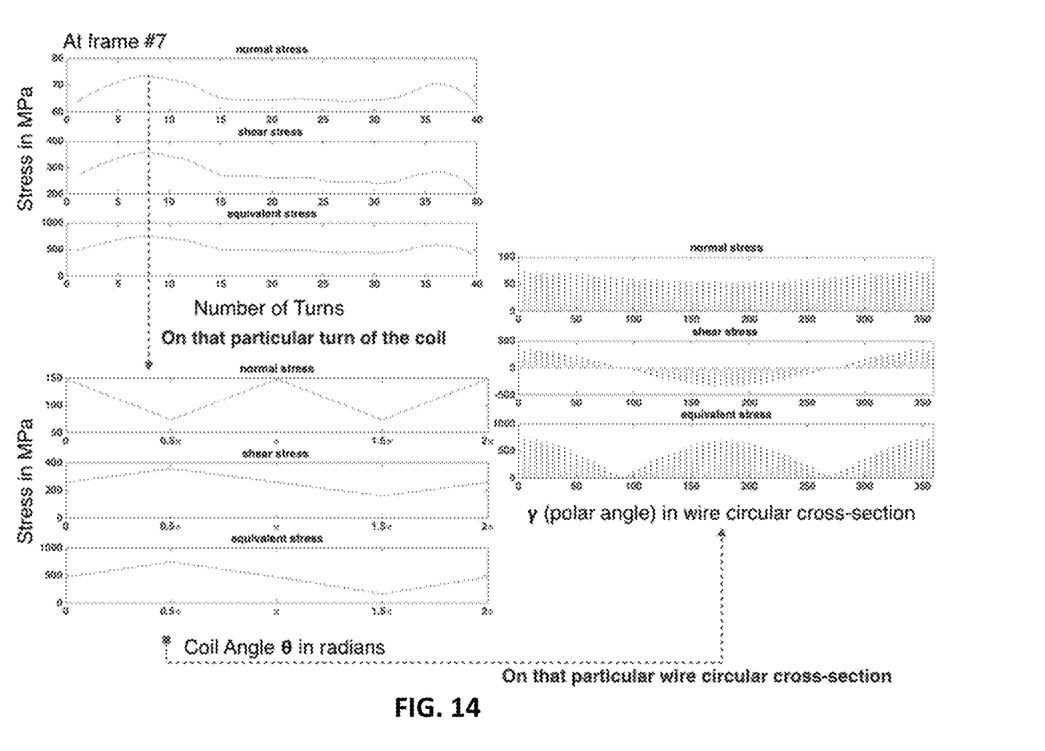
FIG. 14 shows the equivalent, normal and shear stress distributions at various rotations.

The maximum equivalent (von Mises) stresses and shear stresses can be found where θ angle is pi/2 (FIG. 14) and at the outer radius of the wire at they angle equals to 0 or 180 degree FIG. 14).

FIG. 14 shows the equivalent stress (von Mises stress), normal stress and shear stress distribution vs. the θ (theta) rotation (turn=8, rx=76.2 μm (wire outer radius), γ=0, frame #7). The equivalent stress (von Mises stress), normal stress and shear stress distribution vs. the γ (gamma) rotation (turn=8, θ=pi/2, rx=76.2 μm (wire outer radius), frame #7). The equivalent stress (von Mises stress), normal stress and shear stress distribution vs. the γ turns (θ=pi/2, di=76.2 μm (wire outer radius), γ=0, frame #7).

Discussion

The analytical method presented here can be used to infer stress in a helical coil lead from readily available radiographic images of a beating heart. It assumes that strains are smoothly distributed among the turns of the coil, which are themselves not individually resolvable in the images.

Inferring Lead Life from Stress Analysis

In the example analyzed here, the strains of the coil were probably influenced by the transepicardial configuration of the lead, resulting in peak stresses that exceeded the safe limit for unlimited cycles of motion. Most of the peak stress arose from the peak curvature in the sigmoidal configuration of the lead. This configuration can only arise if there are substantial translational forces on the anchor points at either end of the coil, i.e. the body of the pacemaker and the myocardial corkscrew electrode. We speculate that the lead would have assumed a much straighter configuration if the system were deployed entirely within the subpericardial space. The analytical method described herein appears to be suited to identifying van Mises stresses that arise from any combination of tensile and bending strains on the helical lead. We assume that a smooth, cylindrical pacemaker body would not impose significant torsional strains on the helical lead.

The maximal allowable stress in the wire itself is likely to depend on the composition of the metal alloy and its method and extent of drawing into the wire from which the coil lead is formed. The amount of drawing required to reach a particular wire diameter significantly affects the material strength and fatigue behaviors [4]. For a miniaturized spring, the fine wire (SS304; wire diameter=152.4 μm) experienced a prolonged process of cold drawing and coiling to that wire diameter and shape. The cold working increases the mechanical strength of the material [4]. For examples, the 844-μm-diameter type 302 stainless steel wires have a yielding stress at 1408 MPa and the ultimate strength at 1911 MPa; the 254-μm-diameter type has ultimate strength at 2240 Mpa. In addition, the mechanical and fatigue property can be further improved if the residual stresses and microcracks were minimized by a heat treatment process (yielding stress increases from 1408 MPa to 1932 MPa when heat treated at 316° C.) [9]. Therefore, the monotonic tensile test is required to find out the true material strength of the used SSL wire in the pacemaker lead.

Adaptive Stabilization by Connective Tissue

In our preliminary animal study, the open-coil leads were found to be embedded in well-organized connective tissue that formed a cylindrical encapsulating sleeve similar to the polymeric sheath of a conventional pacemaker lead. We hypothesize that the trophic factors that stimulate, organize and constantly renew such connective tissues will distribute stress and strain evenly along such tissues, thereby maximizing flexibility and strength. If the lead does not cross anatomical planes, we would expect less flexion strain than we reported herein. If there is a significant bend between the resting orientation of the lead and the fixed ends, it may be possible to induce the connective tissue to distribute the bending strain more evenly. It is common engineering practice to provide a tapering strain relief at the junction between a flexible lead and a large termination. By changing the dimensions of the coil as it approaches such terminations, it may be possible to induce the connective tissue to grow into such a strain-relieving configuration.

In order to obtain long-term functionality of the epicardial micropacemaker system, the flexible lead must accommodate millions of flexion motions. As described above, our epicardial micropacemaker flexible lead is a short open-coil design that is intended to avoid stress-risers that occur when conventional polymeric encapsulants become embrittled and fracture [3, 10-12]. Biological connective tissues tend to have nonlinear stress-strain relationships because of the complex shapes of the proteinaceous filaments from which they are composed. Finite element analysis of the composite material will require a quantitative description of the connective tissue that actually forms around the coils. This could be obtained by comparing the strains produced in the coils when stressed statically in their bare and embedded form. We have successfully used microcomputed x-ray tomography to resolve the individual turns of the coiled leads under such static conditions in vitro. Such methods could be used to investigate systematically how the elastic properties of the composite material changes with factors such as dimensions of the wire coil, polymeric encapsulants with different adhesion to connective tissue, and elution of anti-inflammatory agents such as steroids, which are commonly added to cardiac electrodes to modify the foreign body reaction [ref].

It will be apparent to those skilled in the art that various modifications and variations can be made in the practice of the present subject disclosure and in construction and testing of the coiled lead without departing from the scope or spirit of the subject disclosure. Other embodiments of the subject disclosure will be apparent to those skilled in the art from consideration of the specification and practice of the subject disclosure. It is intended that the specification and examples be considered as exemplary only, with a true scope and spirit of the subject disclosure being indicated by the following claims.

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

ABBREVIATIONS

D=Coil Diameter
R=Coil Radius
d=Wire Diameter
r=Wire radius
C=Spring Index, C=D/d
$\alpha$=Pitch Angle
I=Moment Area of Inertia of the Spring
J=Polar Moment Area of Inertia
E=Modulus of Elasticity
G=Modulus of Rigidity
$\delta$=Elongation
$\rho$=Radius of Curvature
$\kappa = 1/\rho$
$\theta$=Coil rotation angle
$\gamma$=Rotational Angle in the Wire Cross-section
$\beta$=Spring Lateral Flexural Rigidity
$\sigma$=Normal Stress
$\tau$=Shear Stress
$\sigma 1,2$=1st and 2nd Principle stress
$\sigma vm$=von Mises stress

REFERENCES

[1] M. J. Silka and Y. Bar-Cohen, "Pacemakers and implantable cardioverter-defibrillators in pediatric patients," *Heart Rhythm*, vol. 3, pp. 1360-1366, 2006.

[2] G. E. Loeb, L. Zhou, K. Zheng, A. Nicholson, R. A. Peck, A. Krishnan, et al., "Design and Testing of a Percutaneously Implantable Fetal Pacemaker," *Annals of Biomedical Engineering*, vol. 41, pp. 17-27, 2013.

[3] R. PHILLIPS, M. FREY, and R. O. MARTIN, "Long-Term Performance of Polyurethane Pacing Leads: Mechanisms of Design-Related Failures," *Pacing and Clinical Electrophysiology*, vol. 9, pp. 1166-1172, 1986.

[4] A. M. Wahl, *Mechanical springs*: Penton Publishing Company, 1944.

[5] J. M. Meagher and P. Altman, "Stresses from flexure in composite helical implantable leads," *Medical engineering & physics*, vol. 19, pp. 668-673, 1997.

[6] R. C. Juvinall and K. M. Marshek, *Fundamentals of machine component design* vol. 83: John Wiley & Sons New York, 2006.

[7] A. Durelli, V. Parks, and H. Hasseem, "Helices under load," *Journal of Manufacturing Science and Engineering*, vol. 97, pp. 853-858, 1975.

[8] P. A. Altman, J. M. Meagher, D. W. Walsh, and D. A. Hoffmann, "Rotary bending fatigue of coils and wires used in cardiac lead design," *Journal of biomedical materials research*, vol. 43, pp. 21-37, 1998.

[9] S. Bhonsle and C. Van Karsen, "Mechanical and fatigue properties of stress relieved type 302 stainless steel wire," *Journal of Materials Engineering and Performance*, vol. 1, pp. 363-369, 1992.

[10] W. G. de Voogt, "Pacemaker leads: performance and progress," The *American journal of cardiology*, vol. 83, pp. 187-191, 1999.

[11] S. Furman, D. L. Hayes, and D. R. Holmes, *A practice of cardiac pacing*: Wiley-Blackwell, 1989.

[12] E. Podnos, E. Becker, J. Klawitter, and P. Strzepa, "FEA analysis of silicone MCP implant," *Journal of biomechanics*, vol. 39, pp. 1217-1226, 2006.

What is claimed is:

1. A pacemaker, comprising:
a cylindrical electronics package having a longitudinal axis;
a spiral electrode having a longitudinal axis; and
an open coil helical lead having a longitudinal axis and connecting to the electronics package and the spiral electrode;
wherein the longitudinal axis of the open coil helical lead is curved when the open coil helical lead is in a stressed configuration which maintains the longitudinal axes of the electronics package and the spiral electrode in parallel with each other, and wherein the longitudinal axis of the open coil helical lead is straight when the open coil helical lead is in a resting configuration which maintains the longitudinal axes of the electronics package and the open coil helical lead in parallel with each other, and perpendicular to the longitudinal axis of the spiral electrode; and
wherein the open coil helical lead comprises a lead material and a structure which become embedded in living connective tissue thereby forming a composite material that resists stress fatigue from frequent motion.

2. The pacemaker of claim 1, wherein the open coil helical lead has a coating of insulative material which does not affect its flexibility.

3. The pacemaker of claim 2, wherein the insulative material comprises a polymer from the family of polyparaxylylene.

4. The pacemaker of claim 2, wherein the insulative material thickness is 5-30 um.

5. The pacemaker of claim 1, wherein the open coil helical lead comprises spring-like metals.

6. The pacemaker of claim 5, wherein the open coil helical lead comprises stainless steel.

7. The pacemaker of claim 5, wherein the open coil helical lead comprises SS304 stainless steel.

8. The pacemaker of claim 1, wherein the open coil helical lead has an external diameter of 2-5 mm, a lead wire diameter of 0.1-0.3 mm, and a coil having 5-10 turns per centimeter of length.

9. A pacemaker, comprising:
a cylindrical electronics package having a longitudinal axis;
a spiral electrode having a longitudinal axis; and
an open coil helical lead having a longitudinal axis and comprised of a spring-like material coated with an insulative material and connecting to the electronics package and the spiral electrode;
wherein the longitudinal axis of the open coil helical lead is curved when the open coil helical lead is in a stressed configuration which maintains the longitudinal axes of the cylindrical electronics package and the spiral electrode in parallel with each other, and wherein the longitudinal axis of the open coil helical lead is straight when the open coil helical lead is in a resting configuration which maintains the longitudinal axes of the cylindrical electronics package and the open coil helical lead in parallel with each other, and perpendicular to the longitudinal axis of the spiral electrode; and
wherein when implanted in human tissue, the open coil helical lead is sized to allow adjacent tissue to penetrate between its coils to form a composite material that resists stress fatigue.

10. The pacemaker of claim 9, wherein when implanted in human tissue, the open coil helical lead moves substantially with the motion of the adjacent tissue.

11. The pacemaker of claim 9, wherein the open coil helical lead has an external diameter of 2-5 mm, a lead wire diameter of 0.1-0.3 mm, and a coil having 5-10 turns per centimeter of length.

* * * * *